United States Patent [19]

Christidis et al.

[11] 4,450,292

[45] May 22, 1984

[54] DERIVATIVES OF PHENYL ALIPHATIC CARBOXYLIC ACIDS, AND USE THEREOF IN TREATING GASTRIC AND GASTRO-DUODENAL AILMENTS

[75] Inventors: Yani Christidis; Robert Fournex, both of Paris, France

[73] Assignee: Roussel Uclaf, Paris, France

[21] Appl. No.: 368,208

[22] Filed: Apr. 14, 1982

[30] Foreign Application Priority Data

Apr. 17, 1981 [FR] France .................... 81 07801

[51] Int. Cl.$^3$ .............................. C07C 65/03
[52] U.S. Cl. ........................ 562/463; 560/53; 424/308; 424/316; 424/317
[58] Field of Search .............. 562/463; 560/53; 424/308

[56] References Cited

U.S. PATENT DOCUMENTS 3,846,470  11/1974  Raabe et al. ............ 562/463

FOREIGN PATENT DOCUMENTS 1566213  5/1969  France .................... 562/463
2132354  5/1975  France .................... 562/463
1387733  3/1975  United Kingdom ...... 562/463

OTHER PUBLICATIONS

European Journal of Medical Chemistry Chimica Therapeutica, vol. 12.

Chemical Abstracts, vol. 88, No. 5, Jan. 30, 1978, Abstract 37442p.

*Primary Examiner*—Paul J. Killos
*Attorney, Agent, or Firm*—Stevens, Davis, Miller & Mosher

[57] ABSTRACT

A compound of the formula (I)

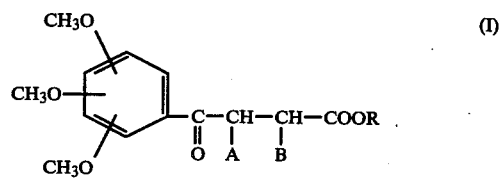

in which the three methoxy radicals are in the 3,4,5, or 2,4,6 or 2,4,5 or 2,3,5 or 2,3,6 positions, in which either A and B together represent a double bond or else A represents a hydrogen atom and B represents a hydroxy radical, and in which R represents a hydrogen atom or an alkyl containing 1 to 5 carbon atoms, in the various possible stereoisomeric forms, as well as the alkali metal, alkaline-earth metal, or amine salts thereof in which R represents a hydrogen atom, methods of producing the same, pharmaceutical compositions containing the same and treatment of various gastric ailments are disclosed.

3 Claims, No Drawings

DERIVATIVES OF PHENYL ALIPHATIC CARBOXYLIC ACIDS, AND USE THEREOF IN TREATING GASTRIC AND GASTRO-DUODENAL AILMENTS

The present invention relates to new derivatives of phenyl aliphatic carboxylic acids, a process of preparing them and their use as drugs in the treatment of gastric and gastro-duodenal ailments, as well as compositions containing them.

Particularly the present invention relates to compounds of the general formula (I)

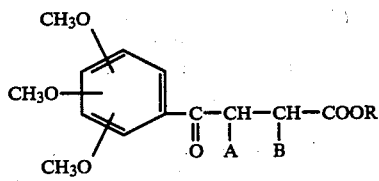

in which the three methoxy radicals are in the 3,4,5 or 2,4,6 or 2,4,5 or 2,3,5 or 2,3,6 positions, in which either A and B together represent a double bond or else A represents a hydrogen atom and B represents a hydroxy radical, and in which R represents a hydrogen atom or an alkyl containing 1 to 5 carbon atoms, in the various possible stereo-isomeric forms, as well as the pharmaceutically acceptable alkali metal, alkaline-earth metal or amine salts of the compound of formula (I) in which R represents a hydrogen atom.

The above compounds of formula (I) show substantial anti-ulcer activity. When placed in contact with the gastric mucosa, they exhibit a gastric anti-secretory and cytoprotective activity. They are useful for the treatment of hyperchlorhydria, gastric and gastro-duodenal ulcers, gastritis, hiatal hernias and gastric and gastro-duodenal ailments accompanied by gastric hyperacidity.

The expression "alkyl containing 1 to 5 carbon atoms" may, for instance, designate a methyl, ethyl, n-propyl, iso-propyl, n-butyl, isobutyl, tertbutyl or pentyl radical.

The different possible stereoisomeric forms represent, for compounds of formula (I) in which A and B together represent a double bond, the geometric isomers E and Z (trans and cis) and in the case of the compound of formula (I) in which A represents a hydrogen atom and B represents a hydroxy radical, the various racemic and optically active forms of these compounds.

The alkali metal or alkaline-earth metal salts of the compound of formula (I) in which R represents a hydrogen atom may for instance be the sodium, potassium, lithium or calcium salts.

The amine salts of compounds of formula (I) in which R represents a hydrogen atom are the customary amine salts. Among the customary amines mention may be made of monoalkyl amines, such as, for instance, methylamine, ethylamine and propylamine; dialkylamines such as, for example, dimethylamine, diethylamine and di-n-propylamine; and trialkylamines such as triethylamine. Mention may also be made of piperidine, morpholine, piperazine and pyrrolidine.

More particularly, the invention has as its object:
compounds as defined by formula (I) above in which A and B together represent a double bond in the form of E or Z isomers, as well as the alkali metal, alkaline-earth metal or amine salts of the said compounds of formula (I) in which R represents a hydrogen atom;

compounds as defined by formula (I) above in which A and B together represent a double bond in the form of E isomers, as well as the alkali metal, alkaline-earth metal or amine salts of the said compounds of formula (I) in which R represents a hydrogen atom;

compounds as defined by formula (I) above in which the three methoxy radicals are in the 3,4,5 or 2,4,5 position in the form of E isomers, as well as the alkali metal, alkaline earth metal or amine salts of the said products of formula (I) in which R represents a hydrogen atom.

Among the compounds of the invention, more particular mention may be made of:

-(E)-4-(3,4,5trimethoxy phenyl)-4-oxo-2-butenoic acid; and

-(E)-4-(2,4,5-trimethoxy phenyl)-4-oxo-2-butenoic acid.

In accordance with the invention, the compounds of formula (I) above in the different possible stereoisomeric forms as well as the alkali metal, alkaline-earth metal or amine salts of the said products of formula (I) in which R represents a hydrogen atom may be prepared by a process characterized by reacting glyoxylic acid or one of its alkyl esters of formula (II)

in which R represents a hydrogen atom or an alkyl containing form 1 to 5 carbon atoms, with an acetophenone of formula (III)

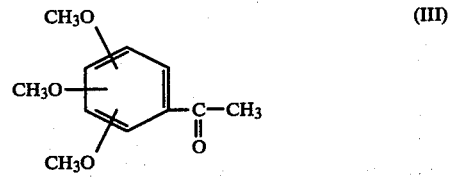

in which the methoxy radicals have the positions indicated above, in order to obtain a compound of formula $I_A$ corresponding to a compound of formula I in which A represents a hydrogen atom and B represents a hydroxy radical, or a compound of formula $I_B$ corresponding to a compound of formula (I) in which A and B together represent a double bond of (E) configuration and, if necessary, subjecting a compound of formula $I_A$ to a dehydration agent in order to obtain a corresponding compound of formula $I_B$ of (E) configuration and, if desired, splitting a resultant compound of formula $I_A$ into its optically active isomers and, if desired, isomerizing a compound of formula $I_B$ of (E) configuration into a compound of formula $I_B$ of (Z) configuration and, if desired, salinifying or esterifying a resultant compound of formula (I), in which represents a hydrogen atom, by customary methods.

By condensation of a compound of formula (II) and a compound of formula (III), one obtains a compound of formula $I_A$ or a compound of formula $I_B$ or a mixture of these compounds depending on the operating conditions, in particular pH, temperature, and time of heating.

In accordance with the various possible combinations of pH, temperature and time of heating, which are well known to the man skilled in the art of aldolization chemistry, larger or smaller proportions of compound $I_A$ or compound $I_B$ are obtained.

The compounds of formula $I_A$ are always formed first and the compounds of formula $I_B$ derived therefrom by dehydration.

In general, the proportion of compound of formula $I_B$ which is formed directly increases when the operating conditions are such that the medium is more strongly acid (see for instance MATHIEU and ALLAIS, Cahiers de Synthese Organique, Vol. 3, page 102, the passage concerning aldolization chemistry.)

Under the preferred conditions for carrying out the process of the invention, the process described above is carried out as follows:

(a) When it is desired to obtain directly a compound of formula $I_B$ the reaction of the compound of formula (II) and the product of formula (III) is carried out in a strongly acid medium. The acid medium may be obtained, for example, by use of an excess of glyoxylic acid or by the presence of an acid such as hydrochloric acid, sulfuric acid or phosphoric acid, or by the addition of sodium hydrogen sulfonate to the reaction medium.

For the direct preparation of $I_B$ products, one can also operate, for example, in the presence of acetic anhydride at about 130° C. by a process analogous to that described in Japanese patent application 7739020 published on Oct. 3, 1977 (C-A 88, 37442 p) or in J. Med. Chem. 1972, Vol. 15, No 9, 918–22. The glyoxylic acid can even be used if desired in the form of alkali metal salt, such as the sodium or potassium salt.

When it is desired to obtain compounds of formula $I_B$, the condensation of the compound of formula (II) and the compound of formula (III) is preferably carried out at a temperature of between 120° and 150° C. and heating is preferably effected for more than three hours.

It is well-known that the "aldols" dehydrate very easily into corresponding unsaturated derivatives either upon heating or by treating in acid medium and that this dehydration can be effected either in a few minutes at high temperature, as described, for example, in U.S. Pat. No. 3,953,463 (one to two minutes at 155° C.), or at lower temperature for a longer period of time.

(b) When it is desired to obtain compounds of formula $I_A$, the condensation of the compound of formula (II) with the compound of formula (III) is preferably effected at a pH greater than 6. This condensation is preferably carried out at a temperature below 100° C. and preferably with less than three hours of heating.

When the compound of formula (II) in which R represents a hydrogen atom is used, one can also advantageously operate at room temperature in the presence of a catalyst such as an alkaline agent (sodium hydroxide or potassium hydroxide, for example.)

(c) The condensation of the compound of formula (II) and the product of formula (III) can be carried out without solvent or in the presence of a solvent, such as an aromatic or aliphatic hydrocarbon (benzene, toluene or heptane, for example.)

(d) The possible dehydration of a compound of formula $I_A$ into a compound of formula $I_B$ can be effected, for instance, by treatment at an elevated temperature in an acid medium.

Suitable dehydration agents may be, for instance, hydrochloric acid, sulfuric acid, phosphoric acid or an alkali metal hydrogen sulfonate such as sodium or potassium hydrogen sulfonate.

(e) The splitting of the racemic compounds of formula (I) into optically active isomers is effected in accordance with customary methods.

(f) The alkali metal, alkaline-earth metal or amine salts of compounds of formula (I) can be prepared by an ordinary method such as, for instance, the action on the said compounds of formula (I) of the corresponding bases or by a double decomposition reaction or by any customary method known for this type of α, β ethylenic carboxylic acids.

The salinification reaction is preferably carried out in a solvent or mixture of solvents such as water, ethyl ether, acetone, ethyl acetate, tetrahydrofuran or dioxane.

(g) The compounds of formula (I) in which R represents an alkyl radical containing from 1 to 5 carbon atoms can be prepared from compounds of formula (I) in which R represents a hydrogen atom in the customary manner by action of an alcohol of formula ROH, preferably in acid medium. The acid may, for instance, be hydrochloric acid, phosphoric acid or paratoluene sulfonic acid.

(h) The compounds of formula (I) in which A and B together represent a double bond, in the form of Z isomers, can be obtained by irradiation of the corresponding compounds of formula (I) in the form of E isomers, by the method described in J. Org. Chem. 13, 1948, pages 284–286.

As indicated above, the compounds of the present invention and pharmaceutical compositions containing the same are useful for the treatment of various ailments listed above.

The dose, which varies in accordance with the compound used and the ailment in question, may range, for instance, between 0.05 and 2 g/day for adults, by mouth.

The pharmaceutical compositions of the present invention which contain at least one compound of formula (I) as an active ingredient may be made in such a manner that they can be administered by digestive or parenteral route.

They may be solid or liquid and are in the pharmaceutical forms currently used in human medicine, such as, for instance, simple or coated tablets, capsules, granules, suppositories, and injectable preparations; they are prepared by the customary methods.

The active ingredient or ingredients may be incorporated in excipients customarily employed in these pharmaceutical compositions, such as talc, gum arabic, lactose, starch, magnesium stearate, cocoa butter, aqueous or nonaqueous vehicles, fats of animal or vegetable origin, paraffin derivatives, glycols, the various wetting, dispersing and emulsifying agents and preservatives.

The compounds of formula (II) and (III) are known products.

The examples given below further illustrate the invention without, however, limiting it:

EXAMPLE 1

4-(2,4,5-trimethoxyphenyl)-4-oxo-2-hydroxy butanoic acid 19.3 g of glyoxylic acid of 50% by weight are heated in water under reduced pressure until elimination of about 80% of the water present and then, after cooling, 54.6 g of 2-4-5-trimethoxy acetophenone are introduced into the reaction medium. Heating is effected for three hours at 90° C. under reduced pressure (about 50 mm/Hg), at the same time distilling off the residual water present.

After cooling of the medium, there are introduced 200 cc of toluene and 400 cc of water containing 7.5 g of sodium carbonate.

The aqueous phase is poured off, washed with toluene and then acidified to a pH of 1 with 50% hydrochloric acid. The desired product is then extracted with ethyl acetate. After elimination of the solvent and recrystallization in 200 cc of 1,2-dichloroethane there were obtained 24.6 g of 4-(2,4,5-trimethoxyphenyl)-4-oxo-2-hydroxy butanoic acid. MP=146° C.±1° C.

Analysis: Calculated: C% 54.93; H% 5.67. Found: C% 54.9; H% 5.7.

NMR Spectrum: In agreement with the structure.

Acidimetry: (Expressed in percentage of the theoretical): 100.5±0.5%

EXAMPLE 2

(E) 4-(2,4,5-trimethoxyphenyl)-4-oxo-2-butenoic acid 11 g of 4-(2,4,5-trimethoxyphenyl)-4-oxo-2-hydroxybutanoic acid obtained in Example 1, 30 cc of acetic acid and 2 cc of concentrated hydrochloric acid (d=1.18) are heated under reflux for 2.5 hours.

The resultant solution is then cooled to room temperature and then, after addition of 100 cc of water, the precipitate which has formed is filtered off, giving 7 g of the crude expected product. MP=207°-208° C.

After recrystallization from 20 cc of acetic acid, 6.3 g of the pure expected product are obtained. MP=210° C.

Analysis: Calculated: C% 58.64; H% 5.30. Found: C% 58.6; H% 5.3.

NMR Spectrum: The coupling constant of the vinyl protons is 16 Hz, which indicates transisomerism.

EXAMPLE 3

4-(3,4,5-trimethoxyphenyl)-4-oxo-2-hydroxy butanoic acid 29.6 g of glyoxylic acid of 50% by weight are heated in water under reduced pressure until elimination of 80% of the water present, whereupon, after cooling, 84.1 g of 3,4,5-trimethoxy acetophenone are introduced into the reaction mixture. Heating is effected for two hours at 95°-100° C. under reduced pressure (about 50 mm/Hg), at the same time distilling off the residual water present.

After cooling of the medium, 120 cc of water containing 11.6 g of sodium carbonate and ether are introduced, the aqueous phase is decanted and washed with ether, whereupon the aqueous phase is acidified to a pH of 1 with 50% hydrochloric acid.

The desired product is extracted with ethyl acetate. After elimination of the extraction solvent and recrystallization from 1,2-dichloroethane, 31.5 g of the expected product are obtained. MP=119°-120° C.

Analysis: Calculated: C% 54.93; H% 5.67. Found: C% 54.9; H% 5.7.

Acidimetry: (expressed in percentage of the theoretical): 98.3%

EXAMPLE 4

(E)-4-(3,4,5-trimethoxyphenyl)-4-oxo-2-butenoic acid 15.8 g of 4-(3,4,5-trimethoxyphenyl)-4-oxo-2-hydroxy butanoic acid obtained in Example 3, 20 cc of acetic acid and 20 cc of concentrated hydrochloric acid (d−1.18) are heated for 2.5 hours under reflux.

The reaction medium is cooled and precipitated by water.

The precipitate formed is filtered off. 12 g of the crude expected product are obtained. MP=140° C.

After recrystallization from 40 cc of a 1:1 ethanol:water mixture, 10.5 g of pure expected product are obtained. MP=144° C.

Analysis: Calculated: C% 58.64; H% 5.30. Found: C% 58.4; H% 5.3.

Acidimetry: (expressed in percentage of the theoretical): 98.7±0.5%.

NMR Spectrum: The coupling constant of the vinyl protons is 16 Hz, which indicates transisomerism.

EXAMPLE 5

(E)-4-(2,4,6-trimethoxyphenyl)-4-oxo-2-butenoic acid 3.3 g of potassium hydroxide in pellets are mixed in 100 cc of absolute ethanol, whereupon 31.5 g of 2,4,6-trimethoxy acetophenone are added and then, within the course of 30 minutes at 20° C., drop by drop a solution of 4.6 g of 80% glyoxylic acid in water in 50 cc of absolute ethanol.

The resultant solution is then heated for six hours under reflux and then evaporated to dryness under reduced pressure. The residue is taken up in 300 cc of water, filtered, and the filtrate collected and acidified to a pH of 1 with concentrated hydrochloric acid. The desired product crystallizes out, is suction filtered and then dried to constant weight at 60° C. under reduced pressure. 0.7 g of expected product is obtained, which is recrystallized from methylethyl ketone. MP=152° C.±1° C.

Analysis: $C_{13}H_{14}O_6$ (266.30): Calculated: C%; 58.64; H% 5.30. Found: C% 58.7; H% 5.5.

NMR Spectrum: The coupling constant of the vinyl protons is 16 Hz, which indicates transisomerism.

EXAMPLE 6

Methyl ester of (E)-4-(3,4,5-trimethoxyphenyl)-4-oxo-2-butenoic acid

A mixture of 20 g of (E)-4-(3,4,5-trimethoxyphenyl)-4-oxo-2-butenoic acid, 150 cc of methanol and 0.15 g of paratoluene sulfonic acid are heated under reflux for five hours. The resultant solution is cooled to room temperature, 0.2 g of sodium acetate is added and evaporation is effected under reduced pressure. 200 cc of toluene are added to the residue, it is washed with an aqueous solution of sodium bicarbonate and then with water. The solvent is removed under reduced pressure, and the residue recrystallized from a 1:1 methanol-water mixture, obtaining 10.7 g of the desired product, melting at 94° C.

EXAMPLE 7

Morpholine salt of (E) 4-(3,4,5-trimethoxyphenyl)-4-oxo-2-butenoic acid 50 cc of ethyl ether containing 1.758 g of morpholine are poured into a solution containing 5.375 g of (E)-4-(3,4,5-trimethoxyphenyl)-4-oxo-2-butenoic acid. The precipitate formed is filtered off, washed with ethyl ether and dried under reduced pressure. One obtains 6.5 g of the desired product melting at 140° C.

EXAMPLE 8

Sodium salt of (E)-4-(3,4,5-trimethoxyphenyl)-4-oxo-2-butenoic acid 28 cc of a 1 N aqueous soda solution are introduced at 10° C. into a mixture of 7.7 g of (E)-4-(3,4,5-trimethoxyphenyl)-4-oxo-2-butenoic acid and 30 cc of water. It is filtered and evaporated under reduced pressure. The resultant solid is taken up in acetone, filtered, washed with acetone and dried under reduced pressure at 20° C. One obtains 7 g of the desired product, melting at 250° C.

EXAMPLE 9

Piperidine salt of (E)-4-(3,4,5-trimethoxyphenyl)-4-oxo-2-butenoic acid 50 cc of ethyl ether containing 1.988 g of piperidine are added to a solution of 6.215 g of (E)-4-(3,4,5-trimethoxyphenyl)-4-oxo-2-butenoic acid in 1200 cc of ethyl ether. The precipitate formed is filtered, washed with ethyl ether, and dried under reduced pressure. There are thus obtained 7.3 g of the desired product, melting at 124° C.

PHARMACEUTICAL FORMS

EXAMPLE 10: TABLETS

Tablets of the following formula were prepared:
-(E)-4-(3,4,5-trimethoxyphenyl)-4-oxo-2-butenoic acid: 100 mg
-Excipient q.s. for a finished tablet of: 300 mg
(Details of excipient: lactose, wheat starch, treated starch, rice starch, magnesium stearate, talc.)

EXAMPLE 11: CAPSULES

Capsules of the following formula were prepared:
-(E)-4-(2,4,5-trimethoxyphenyl)-4-oxo-2-butenoic acid: 100 mg
-Excipient q.s. for a finished capsule of: 300 mg
(Details of excipient: talc, magnesium stearate, aerosil.)

PHARMACOLOGICAL STUDY (1) Determination of the anti-ulcer activity of the compounds of Examples 1 to 4

The technique used is described by SHAY et al in Gastroenterology, 5, 43, (1945).

SHAY'S technique consists in inducing ulcers in rats at the level of the stomach by ligating of the pylorus.

The animals are anesthetized with ether. A longitudinal incision is made about 1 cm below the sternum, the glandular portion of the stomach and the duodenum are exposed and a ligature is applied a few millimeters below the pylorus. The muscular layer is left as is and the skin is sutured by two clips.

The animals immediately receive the dispersant or the substance to be studied by mouth in a volume of 0.5 cc per hundred grams and are kept without food or drink until sacrificed by carotic venesection, effected about 16 hours after the treatment.

Before removing the stomach, a ligature is placed around the cardia.

The gastric fluid is collected in order to measure the pH thereof.

The stomach is then opened along the greater curvature, rinsed in physiological serum and spread out on millimeter paper in order to be examined under a binocular lens.

The seriousness of the lesions is evaluated macroscopically, being rated from 0 to 4 for each stomach.

For each lot of rats the average intensity of the ulcerations is determined and the protection calculated by referring the average index of the group to the average index of the control group.

The pH values of the gastric liquid are also determined for the treated animals and the control animals.

The following results were obtained:

| Compound of Example | Dose (mg/kg) | pH of the Gastric Fluid | | Ulcerization % Protection As Compared with the Controls |
|---|---|---|---|---|
| | | Treated Animals | Control Animals | |
| 1 | 100 | 2.5 | 2.3 | 43 |
| 2 | 20 | 4.6 | 3.2 | 100 |
|   | 4 | 3.6 | 3.2 | 72 |
| 3 | 100 | 3.7 | 2.7 | 45 |
| 4 | 20 | 2.4 | 1.8 | 98 |
|   | 4 | 3.0 | 1.2 | 65 |
|   | 0.8 | 1.8 | 2.3 | 38 |

(2) Determination of the anti-ulcer activity of the compounds of Examples 7 and 8

The technique used is described by SHAY et al in Gastroenterology, 5, 43 (1945) as modified by P. H. Guth in Gastroenterology, 76, 88 (1976).

After 48 hours fast, rats receive the dispersant or the substance to be studied orally in a volume of 1 cc/100 g.

One hour later the animals are anesthetized with ether. A longitudinal incision is made about 1 cm below the sternum, the glandular part of the stomach and the duodenum are exposed and a ligature is placed a few millimeters below the pylorus. The muscular layer is sutured and the skin is clipped.

An hour later, 200 mg/kg of aspirin dispersed in a 1% suspension of methyl cellulose in water to which 150 millimoles of hydrochloric acid have been added are administered orally in a volume of 0.5 cc/100 g.

Two hours after this last administration, the animals are sacrificed by means of carbon dioxide.

Before removing the stomach, a ligature is placed above the cardia.

The gastric fluid is collected in order to measure its pH for the treated animals and the control animals.

The following results were obtained:

| Product of Example | Dose (mg/kg) | pH of the Gastric Fluid | |
|---|---|---|---|
| | | Treated Animals | Control Animals |
| 7 | 100 | 4.1 | 2.0 |
| 7 | 20 | 2.4 | 1.8 |
| 7 | 4 | 2 | 2.3 |
| 8 | 100 | 4.6 | 2.3 |
| 8 | 20 | 3 | 2.4 |
| 8 | 4 | 2.2 | 2.1 |
| 8 | 0.8 | 2.3 | 2.4 |

(3) Determination of the acute toxicity

The $LD_{50}$ lethal dose of the derivatives of Examples 1 to 9 after administration orally to mice was evaluated. The results obtained were as follows:

| Product of Example | LD$_{50}$ (mg/kg) |
| --- | --- |
| 1 | 1000 |
| 2 | 600 |
| 3 | 1000 |
| 4 | 600 |
| 5 | 200 |
| 7 | >400 |
| 8 | >400 |
| 9 | >400 |

What is claimed is:

1. A compound selected from the group consisting of 4-(3,4,5-trimethoxyphenyl)-4-oxo-2-butenoic acid, and pharmaceutically acceptable alkali metal, alkaline-earth metal, and amine salts thereof.

2. A pharmaceutical composition for the treatment of hyperchlorhydria, gastric and gastro-duodenal ulcers, gastritis, hiatal hernias and gastric and gastro-duodenal ailments accompanied by gastric hyperacidity, comprising as the active ingredient an anti-ulcer and anti-gastric secretory effective amount of a compound or salt thereof as defined in claim 1.

3. A method of treating a patient suffering from hyperchlorhydria, gastric or gastro-duodenal ulcers, gastritis, hiatal hernia, or gastric or gastro-duodenal ailments accompanied by gastric hyperacidity, comprising administering to said patient an anti-ulcer and anti-gastric secretory effective amount of a compound or salt thereof as defined in claim 1.

* * * * *